United States Patent
Katkov et al.

(10) Patent No.: US 9,557,090 B2
(45) Date of Patent: Jan. 31, 2017

(54) METHOD AND SCALABLE DEVICES FOR HYPER-FAST COOLING

(75) Inventors: Igor Katkov, San Diego, CA (US); Vladimir Fedorovich Bolyukh, Kharkov (UA); Valery Sergeevich Lupikov, Kharkov (UA)

(73) Assignee: Celltronix, San Diego, CA (US)

(*) Notice: Subject to any disclaimer, the term of this patent is extended or adjusted under 35 U.S.C. 154(b) by 886 days.

(21) Appl. No.: 13/441,004

(22) Filed: Apr. 6, 2012

(65) Prior Publication Data

US 2012/0255313 A1    Oct. 11, 2012

Related U.S. Application Data

(60) Provisional application No. 61/472,308, filed on Apr. 6, 2011.

(51) Int. Cl.
  *F25B 19/00*   (2006.01)
  *F25D 3/10*    (2006.01)
  *A01N 1/02*    (2006.01)

(52) U.S. Cl.
  CPC ............. *F25D 3/102* (2013.01); *A01N 1/0257* (2013.01); *A01N 1/0268* (2013.01); *A01N 1/0289* (2013.01); *F25D 2400/30* (2013.01)

(58) Field of Classification Search
  CPC . F25D 3/10–3/105; F25D 3/11; A01N 1/0242; A01N 1/0252; A01N 1/0257; F17C 2227/045
  USPC .................. 62/62, 63, 65, 614, 64, 54, 51.1
  See application file for complete search history.

(56) References Cited

U.S. PATENT DOCUMENTS

| | | | | | |
|---|---|---|---|---|---|
| 3,815,377 | A | * | 6/1974 | Tyree, Jr. | 62/62 |
| 4,030,314 | A | * | 6/1977 | Strehler et al. | 435/1.3 |
| 4,107,937 | A | * | 8/1978 | Chmiel | 435/1.3 |
| 4,852,358 | A | * | 8/1989 | Acharya | A23L 3/361 62/374 |
| 5,024,830 | A | * | 6/1991 | Linner | 435/40.52 |
| 5,321,955 | A | * | 6/1994 | Leonard | 62/51.1 |
| 5,365,752 | A | * | 11/1994 | Coffre | A23L 3/362 62/266 |

(Continued)

FOREIGN PATENT DOCUMENTS

WO    WO 2006007884 A1 *   1/2006 ............... B01L 1/00

OTHER PUBLICATIONS

Ultra-rapid vitrification of mouse oocytes in low cryoprotectant concentrations; Ho-Joon Lee, Heidi Elmoazzen, Diane Wrightl, John Biggers, Bo R Rueda, Yun Seok Heo, Mehmet Toner, and Thomas L Toth; Published in final edited form as: Reprod Biomed Online. Feb. 2010 ; 20(2): 201. doi:10.1016/j.rbmo.2009.11.012.; NIH Public Access.*

(Continued)

*Primary Examiner* — Len Tran
*Assistant Examiner* — Gordon Jones
(74) *Attorney, Agent, or Firm* — Thibault Patent Group (57) ABSTRACT

A method for hyper-fast cooling of samples is described. The samples are secured in a sample container, then the sample container inserted into a cryogenic cooling chamber through an opening of the cooling chamber. The sample container is placed some distance away from a cooling head, but within range of a continuous stream of pressurized liquid coolant emitted by the cooling head, where, the sample is hyper-cooled by spraying the sample container with a continuous stream of the pressurized liquid coolant.

19 Claims, 9 Drawing Sheets

(56) References Cited

U.S. PATENT DOCUMENTS

| | | | | |
|---|---|---|---|---|
| 5,385,307 A * | 1/1995 | Azar | ................ | B29B 17/0206 241/41 |
| 6,742,144 B2 * | 5/2004 | Co | ................ | 714/42 |
| 6,877,327 B2 * | 4/2005 | Newman | ................ | F25D 3/11 62/374 |
| 7,059,849 B2 * | 6/2006 | Sakata et al. | ................ | 432/233 |
| 7,082,778 B2 * | 8/2006 | Patel et al. | ................ | 62/259.2 |
| 7,162,888 B2 * | 1/2007 | Shu et al. | ................ | 62/378 |
| 7,197,884 B2 * | 4/2007 | Jones et al. | ................ | 62/86 |
| 8,739,556 B2 * | 6/2014 | Yoshimura | ................ | A01N 1/0257 62/378 |
| 2002/0112491 A1 * | 8/2002 | Malone | ................ | F28D 15/06 62/171 |
| 2006/0196627 A1 * | 9/2006 | Shedd et al. | ................ | 164/371 |
| 2007/0169488 A1 * | 7/2007 | Oh | ................ | B01L 1/00 62/62 |
| 2007/0267419 A1 * | 11/2007 | Fuhr | ................ | A01N 1/02 220/592.2 |
| 2008/0216486 A1 * | 9/2008 | Hughes et al. | ................ | 62/47.1 |
| 2009/0011505 A1 * | 1/2009 | Leunissen | ................ | 435/374 |

OTHER PUBLICATIONS

WO_2006007884_A1_I machine translation.*
Vitrification and levitation of a liquid droplet on liquid nitrogen; Young S. Songa, Douglas Adlera, Feng Xua, Emre Kayaalpb,2, Aida Nureddinc, Raymond M. Anchanc, Richard L. Maasd, and Utkan Demircia,; Edited by Daniel D. Joseph, University of Minnesota, Minneapolis, MN, and approved Jan. 13, 2010.*

* cited by examiner

METHOD AND SCALABLE DEVICES FOR HYPER-FAST COOLING

CROSS-REFERENCES TO RELATED APPLICATIONS

The present application claims priority from U.S. Provisional Application Ser. No. 61/472,308 filed on Apr. 6, 2011, which is hereby incorporated herein by reference in its entirety.

TECHNICAL FIELD

The present invention, in some embodiments thereof, relates to hyper-fast cooling of samples. More specifically, the present invention relates to the cryogenic preservation of biological cells via cooling down to the liquid nitrogen temperature in medicine, animal husbandry, and biomedical science. Some embodiments relate to fast cooling of certain electronic equipments such as computer apparatuses, to fields in metallurgy for achieving the glassy state of metals and metals alloys, and to other related fields where hyper-fast cooling of small samples is desirable. More particularly, the invention relates to, but not limited to, devices and methods for hyper-fast cooling for vitrification of biological cells, which will be the major field discussed in the Application.

BACKGROUND OF THE INVENTION

Vitrification is a process when a liquid or semi-liquid biological sample becomes highly viscous, avoiding intracellular and intercellular ice formation and thus, increasing chances for survival; an amorphous vitreous (glassy) phase is formed. This glassy state may be achieved in most liquids by means of very fast cooling. Thus, for example, pure water vitrification is achieved at the cooling rate of about $10^8$ K/min. Utilization of cryoprotective agents (CPAs) significantly increases these extremely high cooling rates to rapid (higher 10,000° C./min) or ultra-rapid (ultra-fast) cooling rates (above 10,000° C./min but below 100,000° C./min). This method is very attractive for cryopreservation of biological samples. High concentrations of permeable CPAs must be used for the most widely used methods of equilibrium (slow) and quasi-kinetic vitrification with relatively more rapid rates of cooling, including ultra-rapid (higher than 100,000° C./min but below 250,000° C./min) vitrifcation. Those CPAs, used in equilibrium or quasi-kinetic vitrification, which comprise, but are not limited to, glycerol, dimethyl sulfox-ide (DMSO), ethylene glycol (EG), or propylene glycol (1,2-propane diol, PG) [Katkov et al., 2012], can substantially damage the cells even without vitrification due to either osmotic damage or specific chemical toxicity [Katkov & Pogorelov, 2007; Katkov, 2011].

The Leidenfrost effect (LFE) is a vapor film formation (film boiling) on the site of the contact between the coolant/heater and heated/cooled sample. In the former case, there is heating LFE, which can be observed when a droplet of water is placed on overheated metallic pan. In the latter case, there is cryogenic LFE, when a liquid coolant boils and forms a vapor coating around the cooling sample (which can be both liquid or solid). It is the major factor that substantially impedes the rate of the surface cooling. All the devices referenced above where the samples are immersed into liquid nitrogen or other coolant, have substantially lower cooling rates than as claimed because of the cryogenic LFE.

It would therefore be advantageous to reduce the LFE effect, to improve the efficiency of cooling, and to simultaneously reduce the need for toxic CPAs. Some embodiments of the present invention can achieve these goals with hyper-fast cooling rates (250,000° C./min and higher) by reducing the LEF effect, and by totally eliminating or substantially decrease the use of potentially toxic permeable CPAs mentioned above.

BRIEF SUMMARY OF EMBODIMENTS OF THE INVENTION (1) The present invention relates to, a method for fast cooling of samples comprises: pressurizing a liquid coolant source; securing a sample in a sample container; securing the sample container onto an insertion mechanism; with the insertion mechanism outside a cryogenic cooling chamber, inserting the sample container into the cryogenic cooling chamber through an opening of the cooling chamber; locking the insertion mechanism and securing the sample container in place some distance away from a cooling head, but within range of a continuous stream of pressurized liquid coolant; cooling the sample by spraying the sample container with a continuous stream of pressurized liquid coolant; and retrieving the sample container after cooling.

(2) In a variant, the method for fast cooling of samples comprises obscuring the opening with a barrier to prevent splashing of the liquid coolant.

(3) In a further variant, the barrier comprises a shutter, and the insertion mechanism comprises a swivel arm, and the method for fast cooling of samples comprises synchronizing the opening of the shutter with moving the swivel arm through the opening of the cooling chamber.

(4) In a variant, the method for fast cooling of samples comprises removing gaseous vapor of the liquid coolant and collecting liquid coolant spent in the cooling chamber.

(5) The present invention relates to an apparatus for fast cooling of samples, comprising: a pressurized liquid coolant source; a suction mechanism; a cooling head configured with an inlet connected to the pressurized liquid coolant source, and an outlet connected to the suction mechanism; a cryogenic cooling chamber having an opening, inside which the cooling head is disposed; a sample container, in which samples are secured; and an insertion mechanism, configured to insert the sample container through an opening into the cryogenic cooling chamber, to secure the sample container at some distance from the cooling head during a cooling process, and to retract the sample container after the cooling process is completed.

(6) In a variant, the apparatus comprises a control mechanism, configured to operate the insertion mechanism, the pressurized coolant source and the suction mechanism according to a predetermined sequence.

(7) In another variant, the apparatus comprises a plurality of inlet branches and a plurality of outlet branches in the cooling head. The cooling head comprises a cooling end portion. The cooling end portion defining a region where the inlet branches terminate and the outlet branches commence. The inlet branches and outlet branches each form an angle of between 25 degrees and 75 degrees with a plane defined by where the outermost extent of where either of the inlet branches and outlet branches terminate and commence respectively.

(8) In a further variant, the sample container comprises a planar surface, and the apparatus being configured to position the planar surface of the sample container in close proximity to the cooling head.

(9) In still another variant, the cooling head comprises a plurality of inlet branches and outlet branches that each terminate and commence respectively at a cooling end of the cooling head. The inlet branches are configured in a row comprising a zigzag pattern, and the outlet branches configured in a row comprising a zigzag pattern. The zigzag rows of inlet and outlet branches are spaced apart from one another and individual inlet and outlet branches are paired with each pair oriented toward a reflection point in space, wherein the outlet branch is oriented to receive coolant emitted from the inlet and reflected off the point.

(10) In yet a further variant, the cooling head comprises a plurality of inlet branches and outlet branches that each terminate and commence respectively at a cooling end of the cooling head, the inlet and outlet branches alternating in a circular pattern, with each outlet oriented in the path of a reflection of emitted coolant from an inlet.

(11) In another variant, the cooling head is removable and is attachable to the inlet and outlet fitting. The inlet fitting is connected to the pressurized liquid coolant source and the outlet fitting is connected to the suction mechanism. The cooling head has a network of inlet branches that are configured in fluid communication with the inlet fitting when the cooling head is attached to the inlet fitting. When connected to the inlet fitting, the inlet branches spray coolant away from the cooling head towards the planar surface of the sample container. The cooling head has a network of outlet branches that are configured in fluid communication with the outlet fitting when the cooling head is attached to the outlet fitting, and when connected to the outlet fitting, the outlet branches suck gaseous coolant out of the chamber.

(12) In a further variant, the pressurized coolant source comprises a pressure vessel, comprising a heating element disposed inside the vessel for adjusting the pressure inside of the vessel.

(13) In still another variant, the apparatus comprises a control mechanism, configured to monitor and adjust the pressure to allow for continuous stream of coolant to be discharged through the inlet of the cooling head.

(14) In yet a further variant, the insertion mechanism comprises an swivelable L-shaped arm, configured for holding the sample container in a fixed orientation. The L-shaped arm positioned outside the cooling chamber such that the arm is configured to reach through the opening of the chamber when it is swiveled, and secure the sample container in close proximity to the cooling head.

(15) In a variant, the apparatus comprises first and second cooling heads, each having a plurality of inlets branches connected to the pressurized liquid coolant source, and a plurality of outlets branches connected to the suction mechanism. The first and second cooling heads comprise a cooling end portion. The cooling end portion defines a cooling plane where the inlet branches terminate and the outlet branches commence, wherein the inlet and outlet branches form an acute angle of between 25 degrees and 75 degrees with the cooling plane defined by where the inlet and outlet branches terminate and commence respectively. The cooling plane of the second cooling head is disposed opposite and parallel to the cooling plane of the first cooling head, defining a gap between the planes of the first and second cooling heads, the gap sized and shaped to receive the sample container.

(16) In another variant, an insulating barrier is connected to the opening in the cryogenic cooling chamber, and is biased in a position to cover the opening of the chamber.

(17) In a further variant, the insulating barrier comprises a shutter, having two sections adjacent to one another. A first section is configured to be displaced during the insertion of the sample container, and a second section is configured to secure the L-shaped arm in place after the sample container is inserted into the cooling chamber.

(18) In still another variant, a control mechanism is configured to synchronize the insertion mechanism and the insulating shutter.

(19) In yet a further variant, a secondary coolant vessel collects any overflow of the liquid coolant from the cooling head. The overflow liquid coolant is subsequently recycled back into the pressurized coolant vessel.

(20) In another variant, an apparatus for fast cooling of samples, comprises: a pressurized liquid coolant source; a cooling head configured with a plurality of inlet branches connected to the pressurized liquid coolant source, configured to deliver a continuous laminar flow of coolant out of the inlet branches; a cryogenic cooling chamber having an opening, inside which the cooling head is disposed; a sample container, in which samples are secured; an insertion mechanism, configured to insert the sample container through the opening and into the cryogenic cooling chamber, and secure the sample container at some distance from the cooling head during a cooling process, within the continuous flow of the coolant, and to retract the sample container after the cooling process is completed.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention, in some embodiments thereof, relates to hyper-fast cooling of samples. More specifically, the present invention relates to the cryogenic preservation of biological cells via cooling down to the liquid nitrogen temperature in medicine, animal husbandry, and biomedical science. Some embodiments relates to fast cooling of certain electronic equipments such as computer apparatuses, to fields in metallurgy for achieving the glassy state of metals and metals alloys, and to other related fields where hyper-fast cooling of small samples is desirable. More particularly, the invention relates but not limited to devices and methods for hyper-fast cooling with vitrification of biological cells, which will be the major field discussed in the Application.

Figure 1:
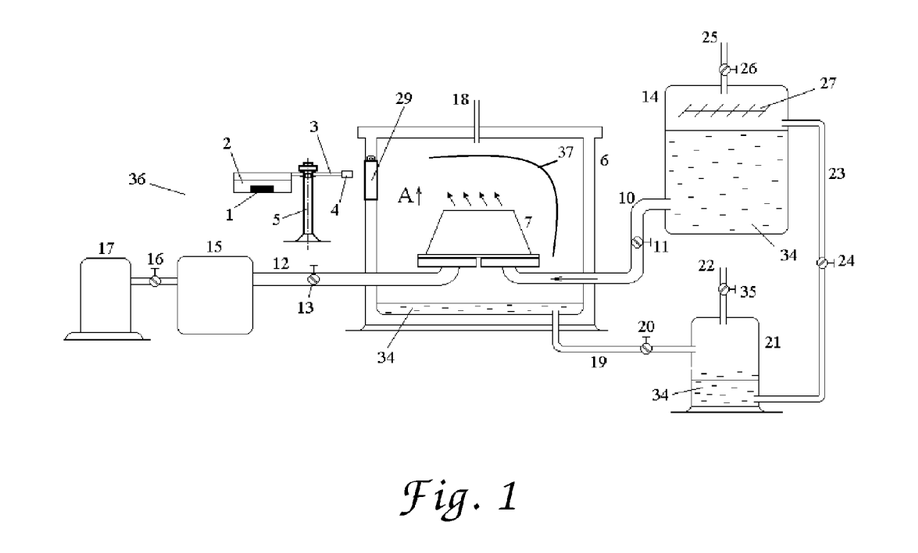
FIG. 1 is a schematic drawing illustrating an apparatus configured for ultra fast cooling of a biological payload immediately before the payload is immersed in a cryogenic cooling chamber. Solid arrows illustrate the direction of pressurized liquid nitrogen flow.
Figure 6:
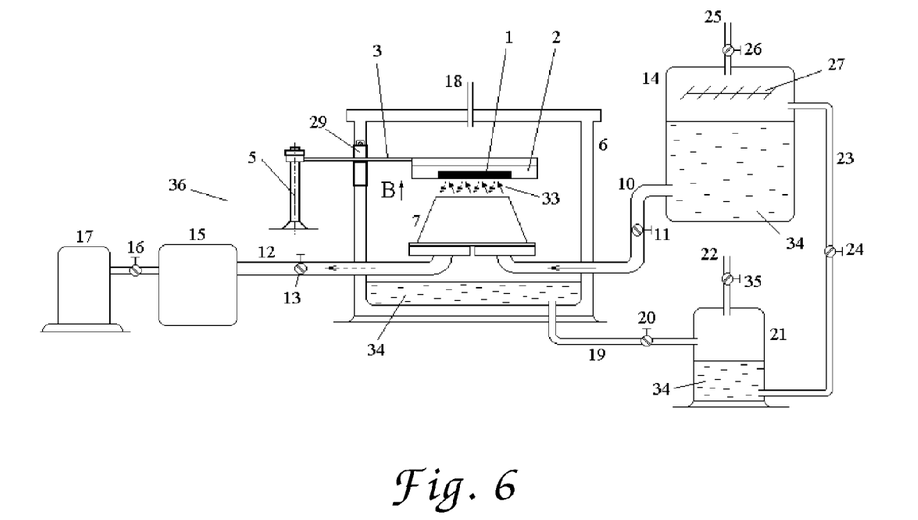
FIG. 6 illustrates a preferred embodiment of the present invention as it cools the biological payload in the cryogenic cooling chamber. Dashed arrows shows the direction of gaseous nitrogen motion.

The following reference numerals are used throughout this document:
1. Biological payload
2. Sample container
3. L-shaped lever
4. Twist knob
5. Stand (vertical or horizontal column)
6. Cryogenic cooling chamber
7. Cooling head
8. Discharge nozzles (Inlet branches)
9. Suction nozzles (Outlet branches)
10. Inlet fitting
11. Inlet valve
12. Outlet fitting
13. Outlet valve
14. Pressurized liquid coolant vessel
15. Depressurized gaseous nitrogen tank
16. Vacuum valve
17. Vacuum pump
18. Vent fitting for the cryogenic cooling chamber
19. Recycle outlet fitting from the cryogenic cooling chamber
20. Valve for 19
21. Assisting or secondary cryostat
22. Vent fitting for the assisting or secondary cryostat
23. Recycle fitting from the assisting or secondary cryostat
24. Valve for 23
25. Vent fitting for the pressurized liquid coolant tank
26. Valve for 25
27. Electric heater
28. Opening along the wall of the cryogenic cooling chamber
29. Master heat insulating shutter
30. Axis around which the master heat insulating shutter turns
31. Secondary shutter
32. Solid bottom of the sample container in contact with liquid coolant 33. Gap between the sample container and the cooling head
34. Liquid coolant, such as nitrogen
35. Valve for 22
36. Room temperature zone
37. Splash shield
38. Cooling plane
39. Angle between the inlet and outlet branches and the cooling plane In a variant, referring to FIG. 1, an apparatus capable of generating high cooling rates for cryogenic preservation of biological cells by vitrification comprises a biological payload 1 (cells in the form of a monolayer), located in flat-ended container 2. The container 2 with biological payload 1 is attached to the end of a L-shaped lever 3 (or insertion mechanism), and has a second end on which there is a twist knob 4. A horizontally located lever 3 is installed on the vertical upright 5 and is configured to turn in a horizontal plane, as shown in FIGS. 1 and 6. In a variant, referring to FIGS. 11-12, the stand up lever 3 is installed on a horizontal column 5 which is configured to turn within a vertical plane.

Figure 2:
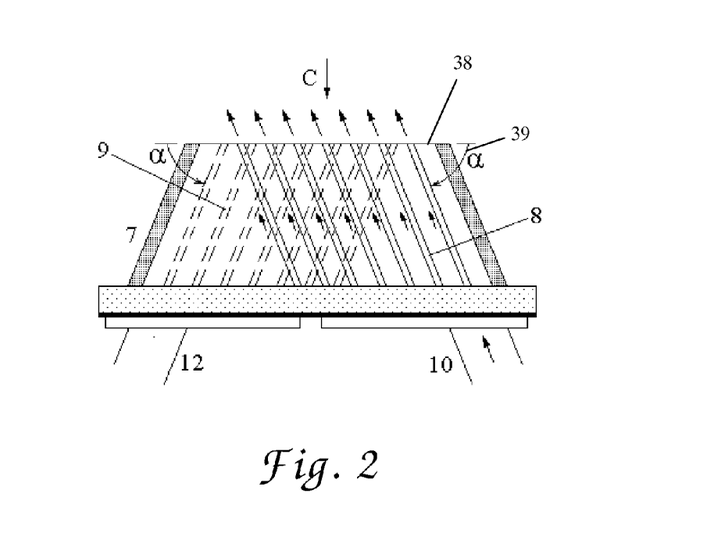
FIG. 2 is a detailed illustration of a cooling head.
Figure 3:
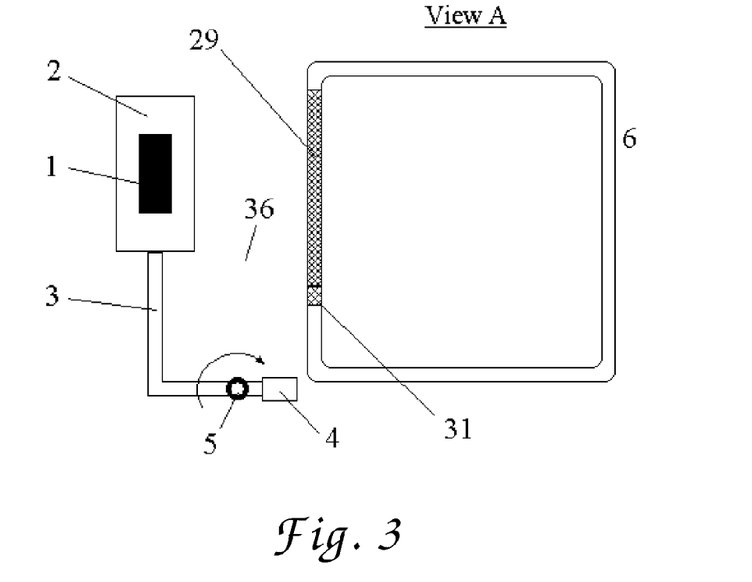
FIG. 3 is a detailed schematic of the insertion mechanism viewed from below. The container with biological payload is attached to the end

Referring to FIG. 1, a cooling head 7 is located in a cryogenic cooling chamber 6, where discharge inlet nozzles (or inlet branches) 8 and outlet suction nozzles (or outlet branches) 9 are installed. An optional splash shield 37 may be provided to reduce splashing of liquid nitrogen. Discharge inlet nozzles 8 and suction nozzles 9 are located at a reflection angle to the surface of container 2. Nozzles are directed to the surface of container 2 at an angle α, which may be between 25 degrees-75 degrees, and preferable between 30 degrees and 45 degrees, as shown in FIG. 2, wherein the process of evaporated nitrogen steam film removal on flat container surface is more effective.

Nozzles are advantageously arranged in the cooling head 7 in such a manner that liquid nitrogen jets of increased pressure emanate from each discharge nozzle 8, reflect from flat-ended container 2, and then the evaporated flow of gaseous nitrogen is removed via the suction nozzle 9.

Discharge nozzles 8 in the cooling head 7 are connected to the inlet fitting 10, where control valve 11 is installed. Suction nozzles 9 of the cooling head 7 are connected to the outlet fitting 12, where control valve 13 is installed. The inlet fitting 10 is connected to a vessel containing pressurized liquid nitrogen 14, and the outlet fitting 12 is connected to a vessel of decreased pressure 15 for removing gaseous nitrogen. Vessel of decreased pressure 15 is connected to vacuum pump 17 through a valve 16.

In the upper part of cryogenic cooling chamber 6 there is a fitting 18 for outlet of evaporated gaseous nitrogen. In the lower part of the cryogenic cooling chamber, a fitting 19 is installed with a control valve 20 so that overflow liquid nitrogen can drain out of the cooling chamber to a secondary cryostat 21. The secondary cryostat 21 is equipped with a fitting 22 for gaseous nitrogen release to the ambient environment, and with an outlet fitting 23 with a valve 24. The outlet fitting 23 is connected to the vessel containing pressurized liquid nitrogen 14 which has outlet fitting 25 with valve 26. An electric heater 27 is located inside the pressurized liquid nitrogen vessel 14.

Figure 4:
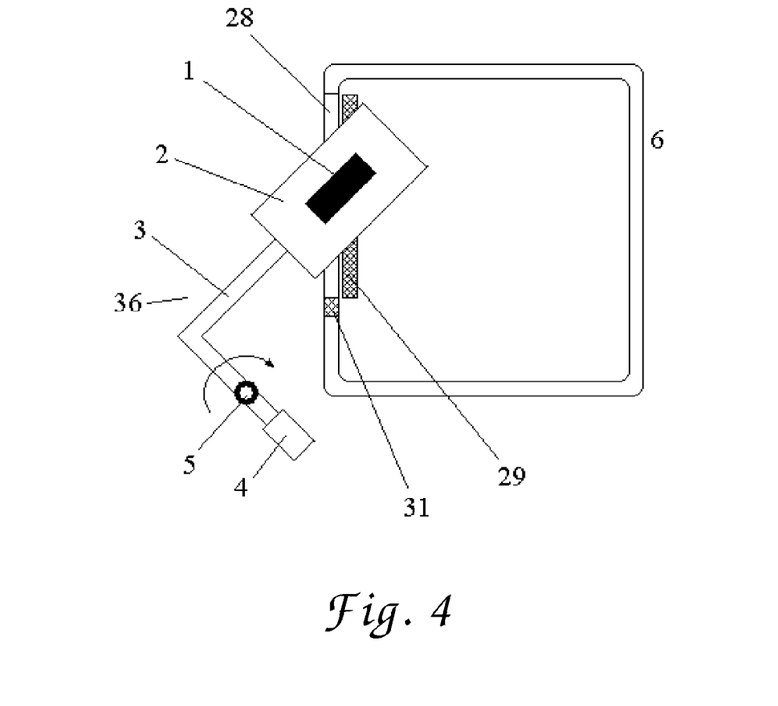
Figure 5:
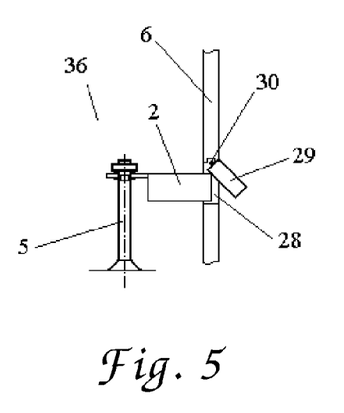
FIG. 5 illustrates the movement of the insulating shield as it is being displace to allow for the insertion of the biological payload from room temperature zone into the cryogenic cooling chamber.

Referring to FIGS. 1, 4 and 6, on one of the side walls of the cryogenic cooling chamber 6, a horizontal opening 28 is made, inside of which a heat insulating shutter 29 is located. In an alternative embodiment, shown in FIGS. 11-12, the vertical opening 28 is made on the top wall of the cryogenic cooling chamber 6, inside of which a spring based heat insulating shutter 29 is located. The horizontal or vertical opening, is generally sized and shaped to conform to and receive the sample container 2.

Figure 11:
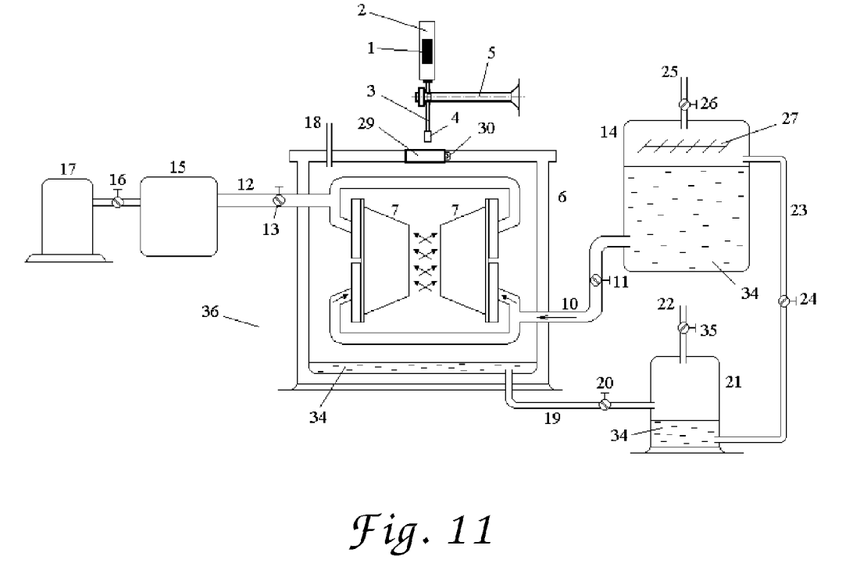
FIG. 11 illustrates a device, providing ultra fast cooling of biological multilayered payload, located in a vertical container, cooled from two sides with two cooling head, before the container with biological payload is inserted into the cryogenic cooling chamber.
Figure 12:
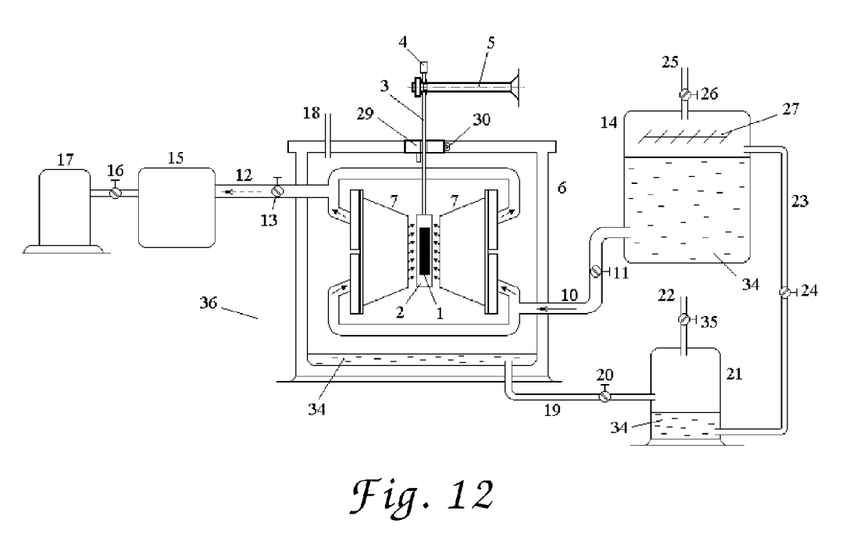
FIG. 12 illustrates the device of FIG. 11 after inserting the container with biological payload into the cryogenic cooling chamber.

The heat insulating shutter 29 is made flat, and in the shape of the opening 28 in the wall of cryogenic cooling chamber 6. The shutter 29 is installed with the capability of turning along an axis 30, adjusted on top (shown in FIG. 1 and FIG. 6), or on the side (as shown in FIG. 11-12) of opening 28. The opening 28 in the tank 6 and flat-ended container 2 are located in one plane. The height and width of the opening 28 are big enough to allow the flat-ended container 2 with biological payload to go through, and is preferably configured with minimal additional space in the opening beyond what would permit the container to pass through.

Figure 8:
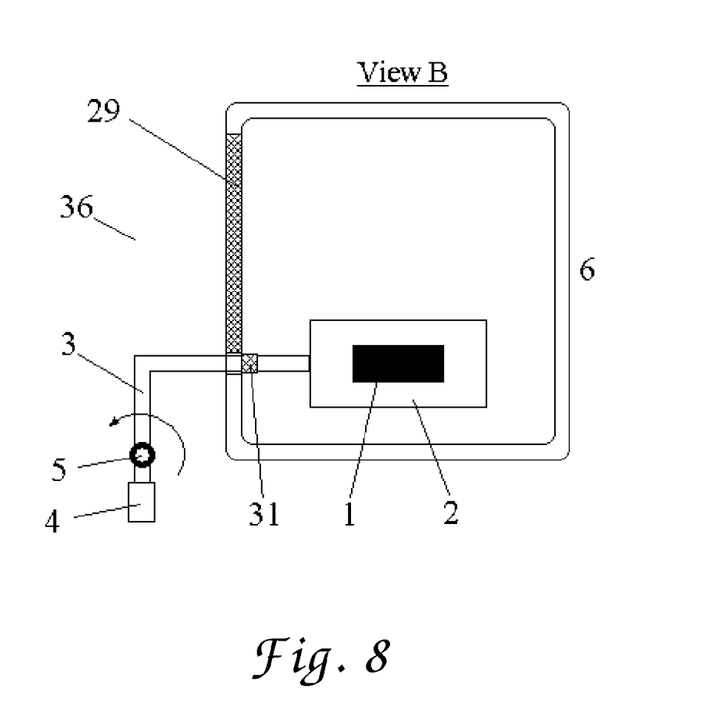
FIG. 8 is a detailed schematic of the container with biological payload after it is transitioned from the room temperature zone into the cryogenic cooling chamber.
Figure 9:
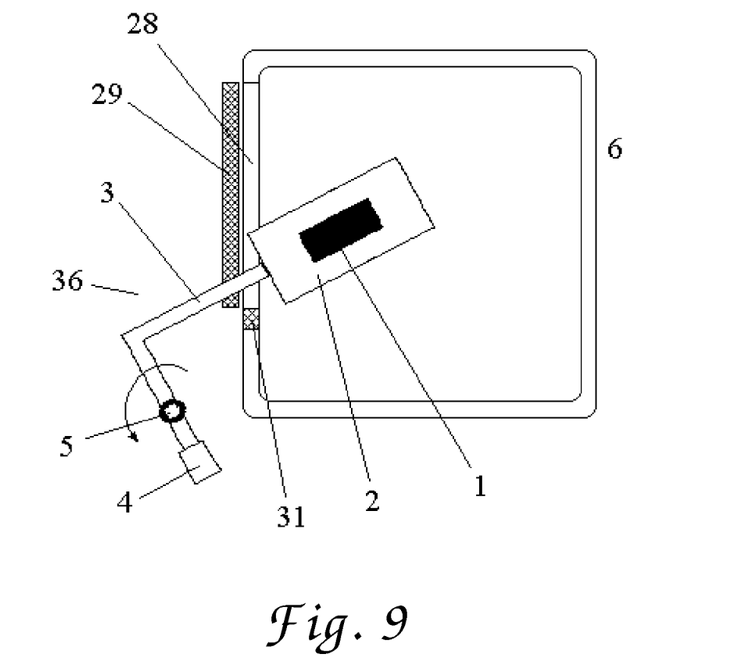
FIG. 9 is a detailed schematic of the moment when the container with biological payload is in the process of being transitioned from the cryogenic cooling chamber back out to the room temperature zone.
Figure 10:
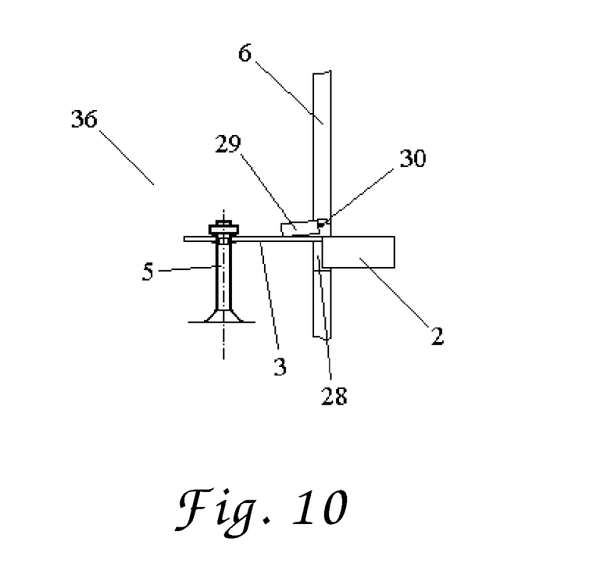
FIG. 10 illustrates the movement of the insulating shield as it is being displace to allow for the biological payload to be removed from the cryogenic cooling chamber back out to the room temperature zone.

In a variant, referring to FIG. 8, the heat insulating shutter is optionally made in two sections: master section 29 and a secondary section 31, configured for both locating the L-shaped lever 3 and fixing the position of the attached container 2 (on lever's end), within cryogenic cooling chamber 6.

Figure 7:
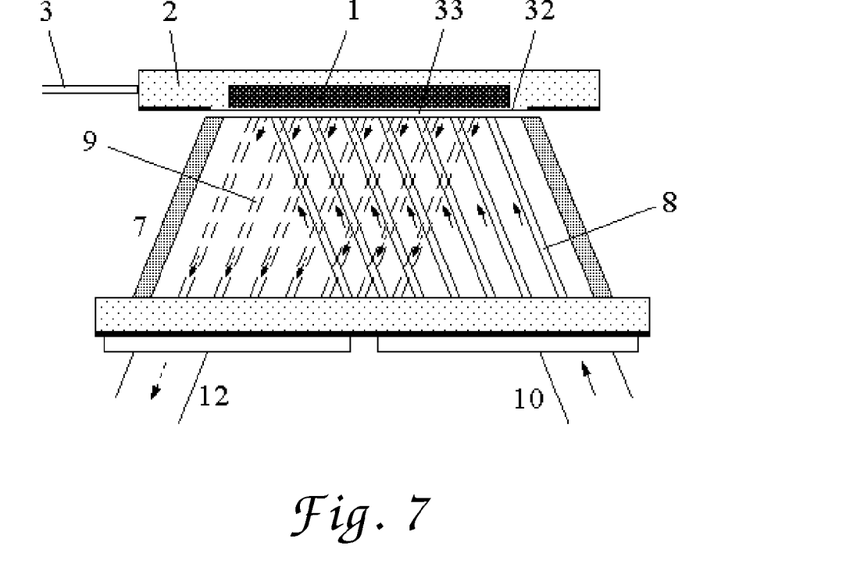
FIG. 7 is a detailed schematic of a cooling head directly beneath and cooling a biological payload.

In another variant, referring to FIG. 7, the solid bottom 32 of the flat-ended container 2 with biological payload 1, on which discharge nozzles 8 and suction nozzles 9 are directed, is made from thin foil of heat conductive material, for example copper or quartz. The solid bottom almost eliminates temperature gradients within the payload 1, while shielding the biological payload from mechanical effects of the liquid nitrogen jet.

Referring to FIGS. 6-7, discharge nozzles 8 and suction nozzles 9 are advantageously arranged in the cooling head 7, to force liquid nitrogen in a in a rapid manner to the sample container 2, and vacuum liquid nitrogen reflected from the container 2, causing a smooth laminar and continuous flow of liquid nitrogen over the container 2. In variant, nozzle 8, 9 endings are located in a plane, parallel to the surface of flat-ended container 2 with biological payload 1. A gap 33 between nozzles 8, 9 endings is formed when the container 2 is brought near the nozzles 8, 9 by the lever 3, but without contacting the nozzles or the cooling head.

Referring to FIG. 1, a suitable liquid coolant, for example, liquid nitrogen 34 with boiling point 77 K, is optionally located in the vessel 14, which is applied to sample container in tank 6 and reused in assisting cryostat 21, which has fitting 22 with valve 35 installed on it. The apparatus may operate in a room temperature zone 36 (~296 K), for example, the room may be where cryogenic cooling chamber 6 and upright 5 with L-shaped lever 3 are located.

Optionally, control valves 11, 13, 16, 20, 24, 26 and 35 can be embodied in electromagnetic form with electronic control.

Figure 17:
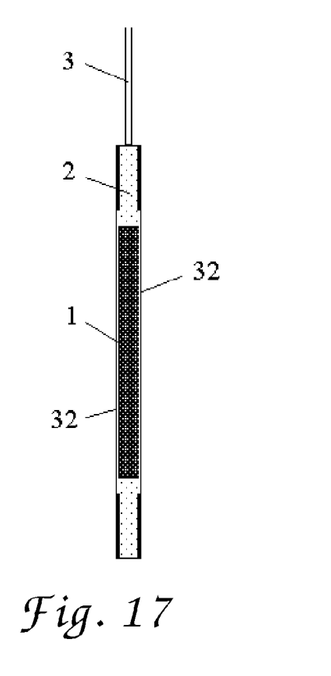
FIG. 17 illustrates a vertically located container with multilayers of biological payload, which will be cooled from both sides.

In still another variant, referring to FIG. 17, the biological payload 1, is formed in the shape of multilayer cells, and upper and lower solid sides 32 of vertical container 2 are optionally made from heat conductive foil. Referring to FIGS. 11-12, two cooling heads 7 are installed opposite one another, are connected to inlet 10 and outlet 12 fittings in parallel, in the cryogenic cooling chamber 6. The heat insulating shutter 29 may be spring based with the capability of turning about a horizontal axis 30, located on the side of the opening in the upper wall of cryogenic cooling chamber 6.

Figure 13:
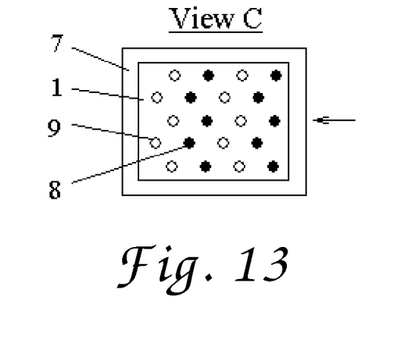
FIG. 13 illustrates a cooling head, viewed from above, that has a rectangular shape, and that the diameter of its inlet tubes is the same as the diameter of the outlet tubes.
Figure 14:
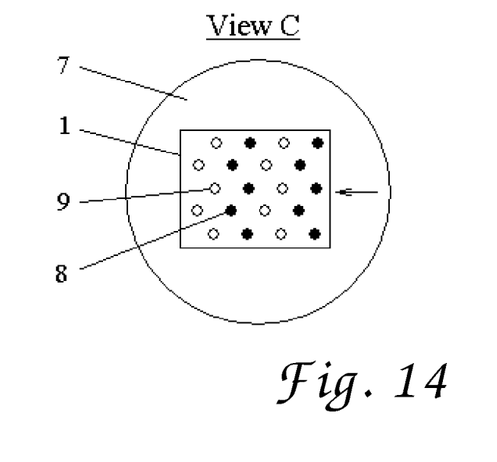
FIG. 14 illustrates a cooling head, viewed from above, that has a round shape, and that the diameter of its inlet tubes is the same as the diameter of the outlet tubes.
Figure 15:
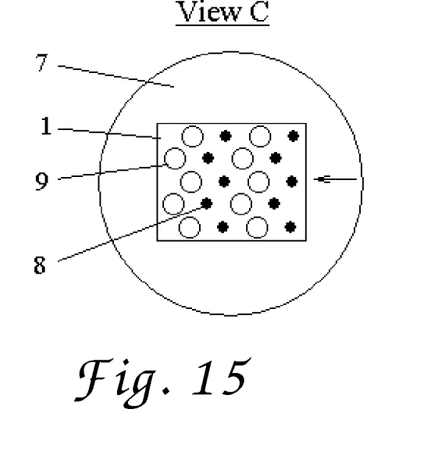
FIG. 15 illustrates a cooling head, viewed from above, that has a round shape, and that the diameter of its inlet tubes is smaller than the diameter of the outlet tubes.
Figure 16:
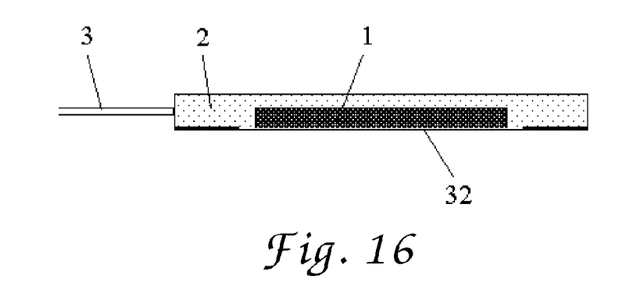
FIG. 16 illustrates a horizontally located container with a monolayer of biological payload, which will be cooled from below.

In yet a further variant, referring to FIG. 13-14, the discharge nozzles 8 and suction nozzles 9 can be made from similar tubes, which can simplify the construction of the apparatus. If the diameter of tubes in suction nozzles 9 is made bigger than the diameter of tubes in discharge nozzles 8, as shown in FIG. 15, then the removal process of gaseous phase from the gap 33 will occur with greater magnitude, which leads to increased cooling rate of biological payload 1.

In operation, the apparatus works as follows. Consider the operation of the device with a horizontally oriented container 2 with biological or other relevant payload 1 in the shape of a very thin layer or monolayer of cells designed for cooling from the lower side, as in FIGS. 1 and 6.

Referring to FIG. 1, in the initial condition, a container 2 with biological payload 1 is located in a room temperature zone 36, and the heat insulating shutter 29 is located vertically in horizontal opening 28 of the side wall of the cryogenic cooling chamber 6.

Valves 24, 26, 11, 13 are closed and valves 16, 20 and 35 are open. At the same time, vacuum pump 17 is providing decreased pressure in vessel 15, and the electric heater 27 is providing increased pressure in the pressure-tight vessel 14 with liquid nitrogen.

Referring to FIGS. 1-2, valve 11 is opened. Under the pressure from the nitrogen vapor, liquid nitrogen 34 flows out of the vessel 14 under pressure through the inlet fitting 10 in the cryogenic cooling chamber 6. At this time liquid nitrogen supplied by the fitting 10 intensively sprays out of discharge nozzles 8 from the cooling head 7.

Referring to FIG. 3, a fast turn of L-shaped lever around the vertical upright 5 is to be carried out by a handle turn 4, which horizontally transfers the flat-ended container 2 with biological payload 1 from the room temperature zone 36 into the cryogenic cooling chamber 6, as shown in FIG. 4. The container 2, while going through the side wall of cryogenic cooling chamber 6, lifts the lower part of the heat insulating shutter 29 by pushing it, which turns relative to the horizontal axis 30, secured at the top of the opening 28 in chamber wall 6, shown in FIG. 5.

Referring to FIGS. 6 and 8, after container 2 is transferred all the way in (not shown) and fixed in position within the cryogenic cooling chamber 6, the master section of the shutter 29 comes back to its initial vertical position, closing or obscuring the opening of the cryostat and preventing intensive liquid nitrogen vapor from leaking into the atmosphere. At this time, the backup section of the shutter 31, in the opening 28 is open where the bolt of L-shaped lever is located, as shown in FIG. 8. The lower solid bottom of the container 2 is exposed to liquid nitrogen flow, originating from the vessel 14 with pressurized liquid nitrogen. Pressurized liquid nitrogen coming out of discharge nozzles 8 of the cooling head 7 is sprays onto the heat conductive foil of film box 2 from a plurality of dispersed jets and thus cools the biological payload 1.

Referring to FIG. 7, after adjusting L-shaped lever 3 to insert container 2 into the cooling chamber 6, faucet 13 is opened. Evaporated gaseous nitrogen is intensively removed from the surface of the cooled container 2 by optional suction nozzles 9. The gaseous nitrogen goes to vessel 15 with decreased pressure via suction nozzles 9 and fitting 12.

As the flow of liquid nitrogen from discharge nozzles 8 is directed at an angle $\alpha$ 39, between 25 degrees and 75 degrees to the flat surface of the container 2, the liquid nitrogen contacts the surface container, then warmed gaseous nitrogen (heated from the warmth from the container) is directed away from each jet (by virtue of being reflected), without interfering with the supply of new liquid nitrogen flowing to the area of the container being cooled. The angle $\alpha$ 39, is also the angle the discharge nozzles and the outlet 9 suctions nozzles make with a cooling plane 38 which is defined as the plane tangent the outmost of nozzles 8, 9.

Given that suction nozzles 9 are directed at the flat surface of container 2 at the same reflection angle as the direction of discharge nozzles, the bulk of vaporized nitrogen is removed (extracted) from the gap 33. In the present cooling method, the vaporized nitrogen film is removed from the surface of container 2 virtually immediately after the beginning of the cooling process. As a consequence, the biological object 1 is subjected to intense cooling in a bubble boiling mode with a high heat transfer coefficient, assuring high cooling rates. Additionally, the high rate of cooling of the biological object 1 is achieved by simultaneous droplet-impact cooling with liquid nitrogen over the entire surface of container 2.

Part of the evaporated gaseous nitrogen from cryogenic cooling chamber 6 will come out through the fitting 18 to the room temperature zone 36, and liquid nitrogen 34 through fitting 19 goes to assisting cryostat 21, where it is accumulated. Evaporated nitrogen also exits to the atmosphere from cryostat 21 through fitting 22.

After cooling of the biological payload 1 to the liquid nitrogen temperature, discharge and suction nozzles are closed by closing the valves 11 and 13.

The L-shaped lever around the vertical upright 5 is turned by the handle 4, and the flat-ended container 2 with biological payload 1 from cryogenic cooling chamber 6 is transferred to room temperature zone 36, as shown in FIG. 9. The container 2, while going through the side wall of the cryogenic cooling chamber 6, lifts lower part of the heat insulating shutter 29 by pushing it, which turns against horizontal axis 30, of attached opening 28 in the upper part of the wall in cooling chamber 6, shown in FIG. 10.

After transition of container 2 to room temperature zone 36 from the cryogenic cooling chamber 6, a master section 29 and secondary section 31 of the shutter comes back to a vertical position, closing the cryostat and preventing further evaporation of liquid nitrogen.

Valve 26 is opened and excessive pressure releases through fitting 25 from the vessel 14 with liquid nitrogen by releasing gaseous nitrogen into room temperature zone 36. Valves 20 and 35 are closed and excessive pressure in secondary cryostat 21 is generated by outer heat flows. Valve 24 is opened and liquid nitrogen 34 from cryostat 21 through fitting 23 goes to vessel 14 due to a pressure difference.

In another variant, referring to FIGS. 11-12, the device operates with the container 2 with biological payload 1 in the shape of a multilayer, located in a vertical plane, similar to as described above. In this case, heat insulating shutter 29 is spring based, which ensures its return to an initial position after turning around the horizontal axis 30, located at the side of the opening 28 in the upper wall of cryogenic cooling chamber 6.

When top and bottom surfaces of the container 2 are cooled by two cooling heads 7 positioned opposite one another, the cooling rate is faster due to a lowering of the temperature gradient over the cross section of biological payload 1.

The apparatus of the present invention can be constructed with or without electromechanical systems, for ease of use in a laboratory environment with regular cryogenic equipment. Apart from the shutter 29, the cooling chamber can be made from firm foam plastic, which can be manufactured relatively cheaply.

Operation of the device is easily performed with the use of electronic circuit diagram, controlling magnetic valves. Handling of the L-shaped lever can be manual, which is convenient for research purposes, or using an electric motor, which is more efficient in mass production of cooled biological payloads.

The consumption of liquid nitrogen is relatively low, which makes the cooling process inexpensive.

In the apparatus of the present invention, high cooling rates of a biological payload may be provided by:

Contact of an ensemble of points over all surface of cooled biological payload is carried out through thin copper or quartz foil directly with cryogenic liquid, instead of steam gaseous heat insulating film;

A very short period of time is provided for the vapor stage (film boiling) on the border of contact of liquid nitrogen with biological payload.

"Impact" removal of the vapor stage by directed motion (under pressure) of liquid nitrogen flow and vacuum suction of formed gaseous nitrogen;

Droplet-impact cooling by mutual contacts of cryogenic liquid with biological payload surface.

Figure 18:
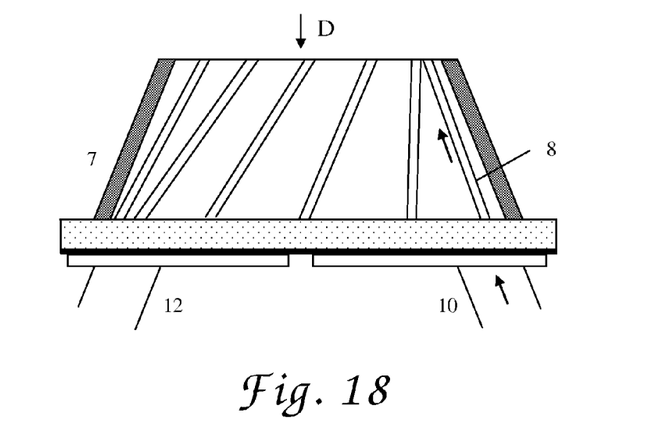
FIG. 18 illustrates an alternative embodiment of the cooling head, where the inlets are located in two planes, parallel to the cooling head's surface, along concentric circles. The endings of the inlets are located along the circumference of a larger diameter. This cooling head can create a "tornado" or "twister" type of the liquid coolant movement.
Figure 19:
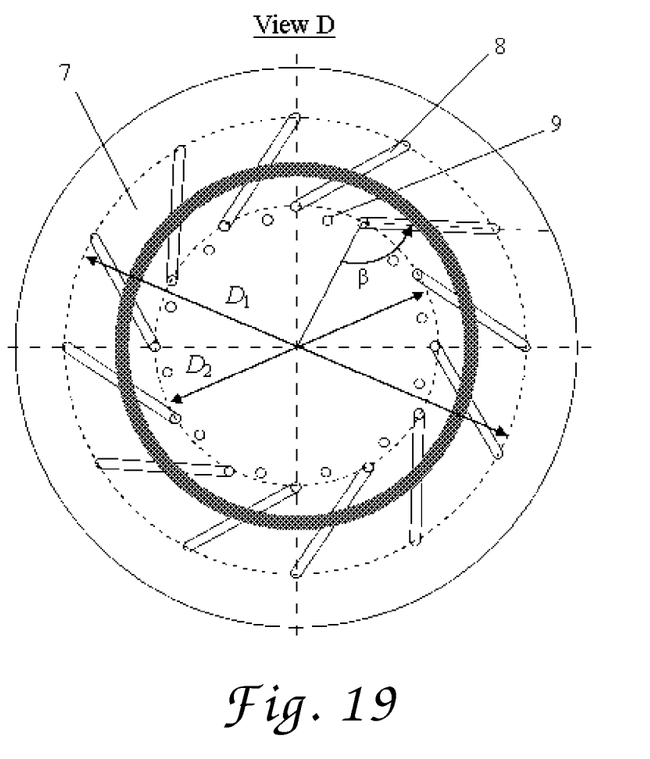
FIG. 19 illustrates the cooling head from FIG. 18 viewed from above.

Another similar but somewhat different device is depicted on FIG. 18, 19. The inlet and outlet endings of the discharge nozzles are located in two planes, parallel to the cold head surface, regularly along concentric circles centered at the axis of the cold head, when inlet endings of discharge nozzles are located along the circumference of a bigger diameter, and the axis of the nozzles are directed past the cold head axis to the inside of a circumference of smaller diameter, on which the outlet endings of the discharge nozzles are located, and the suction nozzle endings are located across the discharge nozzle endings. This device can create a "tornado" or "twister" type of the liquid coolant movement. FIG. 18 illustrates the abovementioned "twister" device, top view D on FIG. 18.

The apparatuses described herein can be scaled up and down to various sizes as needed to suit the size of the sample requiring vitrification.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method for hyper-fast cooling of samples, comprising:
   pressurizing a liquid coolant;
   securing a sample in a sample container;
   securing the sample container onto an insertion mechanism;
   inserting the sample container into a cryogenic cooling chamber through an opening of the cooling chamber;
   locking the insertion mechanism and securing the sample container in place some distance away from a cooling head, but within range of a continuous stream of pressurized liquid coolant;
   cooling the sample at a hyper-fast rate by spraying the sample container with the continuous stream of pressurized liquid coolant from a plurality of inlet nozzles formed into the cooling head, and removing an evaporated flow of gas formed by a warming of the liquid coolant after it has been reflected off of the sample container by a plurality of suction nozzles also formed into the cooling head; and
   retrieving the sample container after cooling.

2. The method for hyper-fast cooling of samples of claim 1, further comprising obscuring the opening with a barrier to prevent splashing of the liquid coolant.

3. The method for hyper-fast cooling of samples of claim 2, wherein the bather comprises a shutter, and the insertion mechanism comprises a swivel arm, and the method further comprising synchronizing the opening of the shutter with moving the swivel arm through the opening of the cooling chamber.

4. An apparatus for hyper-fast cooling of samples, comprising:
   a source of pressurized liquid coolant;
   a cryogenic cooling chamber having an opening, inside which a cooling head is disposed;
   a sample container, in which samples are secured;
   an insertion mechanism, configured to insert the sample container through an opening into the cryogenic cooling chamber, to secure the sample container at some distance from the cooling head during a cooling process, and to retract the sample container after the cooling process is completed; and
   the cooling head, comprising a plurality of inlet nozzles coupled to a source of pressurized liquid coolant for producing a spray of liquid coolant against the sample container, and a plurality of suction nozzles coupled to a suction mechanism and configured to remove an evaporated flow of gas formed by a warming of the liquid coolant as it is reflected off of the sample container.

5. The apparatus of claim 4, further comprising a control mechanism, configured to operate the insertion mechanism, the source of the pressurized coolant and the suction mechanism according to a predetermined sequence.

6. The apparatus of claim 4, wherein the cooling head comprises a cooling end portion, the cooling end portion defining a region where the inlet nozzles terminate and the outlet nozzles commence, wherein the inlet nozzles and outlet nozzles each form an angle of between 25 degrees and 75 degrees with a plane defined by where the outermost extent of where either of the inlet nozzles and outlet nozzles terminate and commence respectively.

7. The apparatus of claim 4, wherein the sample container comprises a planar surface, and the apparatus being configured to position the planar surface of the sample container in close proximity to the cooling head.

8. The apparatus of claim 4, wherein the input nozzles and suction nozzles each terminate and commence respectively at a cooling end of the cooling head, the inlet nozzles configured in a row comprising a zigzag pattern, and the outlet nozzles configured in a row comprising a zigzag pattern;
   wherein the zigzag rows of inlet and outlet nozzles are spaced apart from one another and individual inlet and outlet nozzles are paired with each pair oriented toward a reflection point in space.

9. The apparatus of claim 4, wherein the input and suction nozzles each terminate and commence respectively at a cooling end of the cooling head, the inlet and outlet nozzles alternating in a circular pattern, with each outlet nozzle oriented in a path of a reflection of emitted coolant from the inlet nozzles.

10. The apparatus of claim 4, wherein the cooling head is removable and is attachable to an inlet and an outlet fitting, the inlet fitting being connected to the source of the pressurized liquid coolant and the outlet fitting being connected to the suction mechanism;
    wherein the inlet nozzles are configured in fluid communication with the inlet fitting when the cooling head is attached to the inlet fitting; and
    the outlet nozzles are configured in fluid communication with the source of the pressurized liquid coolant when the cooling head is attached to the outlet fitting.

11. The apparatus of claim 4, wherein the source of pressurized liquid coolant comprises a pressure vessel, comprising a heating element disposed inside the vessel for adjusting the pressure inside of the vessel.

12. The apparatus of claim 11, further comprising a control mechanism, configured to monitor and adjust the pressure to allow for a continuous stream of coolant to be discharged through the inlet nozzles of the cooling head.

13. The apparatus of claim 4, wherein the insertion mechanism comprises a swivelable L-shaped arm, configured for holding the sample container in a fixed orientation, the L-shaped arm positioned outside the cooling chamber such that the arm is configured to reach through the opening of the chamber when it is swiveled, and secure the sample container in close proximity to the cooling head.

14. The apparatus of claim 6, further comprising a second cooling head comprising a second set of inlet nozzles connected to the source of the pressurized liquid coolant, and a second set of outlet nozzles connected to the suction mechanism, wherein the second cooling head comprises a second cooling end portion, the second cooling end portion defining a second cooling plane where the second set of inlet nozzles terminate and the second set of outlet nozzles commence, wherein the second set of inlet and outlet nozzles form an acute angle of between 25 degrees and 75 degrees with the second cooling plane defined by where the second set of inlet and outlet nozzles terminate and commence respectively;
    wherein the second cooling plane is disposed opposite and parallel to the cooling plane of the cooling head, defining a gap between the planes of the cooling head and second cooling head, the gap sized and shaped to receive the sample container.

15. The apparatus of claim 4, further comprising an insulating barrier connected to the opening in the cryogenic cooling chamber, the insulating barrier being biased in a position to cover the opening of the chamber.

16. The apparatus of claim 15, wherein the insulating barrier comprises a shutter, the shutter comprising two sections adjacent to one another;

wherein a first section is configured to be displaced during the insertion of the sample container, and a second section is configured to secure an L-shaped arm of the insertion mechanism in place after the sample container is inserted into the cooling chamber.

17. The apparatus of claim 16, further comprising a control mechanism configured to synchronize the insertion mechanism and the opening and closing of the insulating shutter.

18. The apparatus of claim 4, further comprising a secondary coolant vessel to collect any overflow of the liquid coolant from the cooling head;
wherein the overflow liquid coolant is subsequently recycled back into the source of the pressurized liquid coolant.

19. An apparatus for hyper-fast cooling of samples, comprising:
a source of pressurized liquid coolant;
a sample container, in which samples are secured;
a cooling head configured with a plurality of inlet nozzles connected to the source of the pressurized liquid coolant, configured to deliver a continuous laminar flow of liquid coolant out of the inlet nozzles against the sample container, and a plurality of suction nozzles coupled to a suction mechanism and configured to remove an evaporated flow of gas formed by a warming of the liquid coolant as it is reflected off of the sample container;
a cryogenic cooling chamber having an opening, inside which the cooling head is disposed; and
an insertion mechanism, configured to insert the sample container through the opening and into the cryogenic cooling chamber, and secure the sample container at some distance from the cooling head during an ongoing cooling process, within the extant continuous flow of the coolant, and to retract the sample container after the cooling process is completed.

* * * * *